United States Patent
Stolen et al.

(10) Patent No.: US 10,751,375 B2
(45) Date of Patent: Aug. 25, 2020

(54) MITOCHONDRIAL EPIGENETIC REPROGRAMMING AND TRANSPLANT

(71) Applicant: Boston Scientific Scimed, Inc., Maple Grove, MN (US)

(72) Inventors: Craig M. Stolen, New Brighton, MN (US); Allan Charles Shuros, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 60 days.

(21) Appl. No.: 15/714,166

(22) Filed: Sep. 25, 2017

(65) Prior Publication Data

US 2018/0085407 A1  Mar. 29, 2018

Related U.S. Application Data

(60) Provisional application No. 62/399,566, filed on Sep. 26, 2016.

(51) Int. Cl.
| | |
|---|---|
| *A61K 35/545* | (2015.01) |
| *A61K 35/12* | (2015.01) |
| *C12N 5/074* | (2010.01) |
| *C12N 13/00* | (2006.01) |
| *G01N 33/50* | (2006.01) |

(52) U.S. Cl.
CPC ............ *A61K 35/545* (2013.01); *A61K 35/12* (2013.01); *C12N 5/0696* (2013.01); *C12N 13/00* (2013.01); *C12N 2501/602* (2013.01); *C12N 2501/603* (2013.01); *C12N 2501/604* (2013.01); *C12N 2501/606* (2013.01); *C12N 2506/00* (2013.01); *G01N 33/5079* (2013.01)

(58) Field of Classification Search
CPC .... A61K 35/545; A61K 35/12; C12N 5/0696; C12N 13/00; C12N 2506/00; C12N 2501/602; C12N 2501/606; C12N 2501/604; C12N 2501/603; A61P 9/10; G01N 33/5079
See application file for complete search history.

(56) References Cited

U.S. PATENT DOCUMENTS

| | | |
|---|---|---|
| 7,407,800 B1 | 8/2008 | Benton et al. |
| 8,058,065 B2 | 11/2011 | Yamanaka et al. |
| 2010/0062533 A1 | 3/2010 | Yamanaka et al. |
| 2011/0008310 A1 | 1/2011 | Cataldo et al. |
| 2015/0299658 A1 | 10/2015 | Ma |

FOREIGN PATENT DOCUMENTS

| | | |
|---|---|---|
| WO | 2015192020 | 12/2015 |
| WO | 2018058026 | 3/2018 |

OTHER PUBLICATIONS

Knox et al. Voltage-driven ATP Synthesis by Beef Heart Mitochondrial F0F1-ATPase. JBC (1984), 259(8), 4757-4763. (Year: 1984).*
Zhang et al. UCP2 regulates energy metabolism and differentiation potential of human pluripotent stem cells. The EMBO Journal (2011), 30, 4860-4873. (Year: 2011).*
International Search Report and Written Opinion for PCT Application No. PCT/US2017/053224 dated Dec. 18, 2017 (15 pages).
Masuzawa, Akihiro et al., "Transplantation of autologously derived mitochondria protects the heart from ischemia-reperfusion injury," Am J Physiol Heart Circ Physiol 304; H966-H982, 2013 (17 pages).
Wakiyama, Akihiro et al., "Abstract from Transplantation of Autologously-Derived Mitochondria Protects the Heart from Ischemia-Reperfusion Injury," FASEB Journal, vol. 27, Apr. 2013, p. 1209.7 (2 pages).
Wakiyama, Hidetaka et al., "Selective opening of mitochondrial ATP-Sensitive potassium channels during surgically induced myocardial iscemia decreases necrosis and apoptosis," Eur J Cardio thorac Surg. Mar. 2002; 21(3): 424-433 (19 pages).
International Preliminary Report on Patentability for PCT Application No. PCT/US2017/053224 dated Apr. 4, 2019 (9 pages).
Avalos, Jose "Synthetic Mitochondria," Pioneering Engineering, International Innovation (3 pages).
Bayart, Emilie et al., "Technological Overview of iPS Induction from Human Adult Somatic Cells," Current Gene Therapy, 2013, 13, 73-92 (20 pages).
Bukowiecki, Raul et al., "Mitochondrial Function in Pluripotent Stem Cells and Cellular Reprogramming," Gerontology 2014; 60: 174-182 (9 pages).
Chen, Jenny X. et al., "Somatic Cell Reprogramming ito Cardiovascular Lineages," J Cardiovasc Pharmacol Ther.; 19(4); 340-349 (18 pages).
Cowan, D B. et al., "Intracoronary Delivery of Motchondria to the Ischemic Heart for Cardioprotection," PLoS ONE 11 (1), Aug. 8, 2016 (19 pages).
"Generation of Human induced Plurpotent Stem Cells," Center for iPS Cell Research and Application, iCeMS, Kyoto University, Mar. 2009 (35 pages).
Iacobazzi, Vito et al., "Mitochondrial DNA methylation as a next-generation bioarker and diagnostic tool," Molecular Genetics and Metabolism 110 (2013) 25-34 (10 pages).
Kesner, E. E. et al., "Characteristics of Mitochondrial Transformation into Human Cells," Scientific Reports 6:26057, DOI: 10.1038/srep26057, www.nature.com/scientificreports/ (15 pages).
Maherali, Nimet et al., "Guidelines and Techniques for the Generation of Induced Pluripotent Stem Cells," Cell Stem Cell 3, Protocol Review, Dec. 4, 2008, pp. 595-605 (11 pages).

(Continued)

*Primary Examiner* — Sean C. Barron
(74) *Attorney, Agent, or Firm* — Paul, DeVries Smith & Deffner LLC

(57) ABSTRACT

Embodiments herein include methods for enhancing post-ischemic functional recovery through administration of mitochondria and related devices and methods. In an embodiment, a method for enhancing post-ischemic functional recovery is included. The method can include harvesting somatic cells from a patient or a donor, converting the somatic cells into induced pluripotent stem cells, extracting mitochondria from the induced pluripotent stem cells, and transplanting the mitochondria into the patient. Other embodiments are also included herein.

20 Claims, 5 Drawing Sheets

(56) References Cited

OTHER PUBLICATIONS

Mccully, James D. et al., "Injection of isolated mitochondria during early reperfusion for cardioprotection," Am J Physiol Heart Circ Physiol 296: H94-H105, 2009. (12 pages).

Mccully, James D. et al., "Mitrochondrial transplantation for therapeutic use," Clin Trans Med (2016) 5:16 (13 pages).

Ong, Sang-Bing et al., "New roles for mitochondria in cell death in the reperfused myocardium," Cardiovascular Research (2012) 94, 190-196 (7 pages).

Patananan, Alexander N. et al., "Modifying the Mitochondrial Genome," Abstract Only, Cell Metabolism, (2016) vol. 23, Issue 5, pp. 785-796 (2 pages).

Prigione, Alessandro et al., "Human Induced Pluripotent Stem Cells Harbor Homoplasmic and Heteroplasmic Mitochondrial DNA Mutations While Maintaining Human Embryonic Stem Cell-like metabolic Reprogramming," Stem Cells 2011; 29:1338-1348 (11 pages).

Raab, Stefanie et al., "A Comparative View on Human Somatic Cell Sources for iPSC Generation," Stem Cells International, vol. 2014, Article ID 768391 (13 pages).

Shock, Lisa S. et al., "DNA methyltransferase 1, cytosine methylation, and cytosine hydroxymethylation in mammalian mitochondria," PNAS, Mar. 1, 2011, vol. 108, No. 9, pp. 3630-3635 (6 pages).

Stadtfeld, Matthias et al., "Induced pluripotency: history, mechanisms, and appications," Genes & Development (2010) 24:2239-2263, downloaded from genesdev.cshlp.org on Aug. 23, 2016 (26 pages).

Suhr, Steven T. et al., "Mitochondrial Rejuvenation After Induced Pluripotency," (2010) PLoS ONE 5(11): e14095. (9 pages).

Takahashi, Kazutoshi et al., "A Developmental Framewok for Induced Pluripotency," Development (2015) 142, 3274-3285 (12 pages).

Takahashi, Kazutoshi et al., "Induction of Pluripotent Stem Cells from Mouse Embryonic and Adult Fibroblast Cultures by Defined Factors," Cell 126, 663-676, Aug. 26, 2006 (14 pages).

Xu, Xiuling et al., "Mitochondrial Regulation in Pluripotent Stem Cells," Cell Metabolism 18, Sep. 3, 2013, 325-333 (8 pages).

Response to Communication Pursuant to Rules 161(1) and 162 EPC for European Patent Application No. 17787281.9 filed Nov. 18, 2019 (8 pages).

* cited by examiner

MITOCHONDRIAL EPIGENETIC REPROGRAMMING AND TRANSPLANT

This application claims the benefit of U.S. Provisional Application No. 62/399,566, filed Sep. 26, 2016, the contents of which are herein incorporated by reference in its entirety.

FIELD

Embodiments herein relate to methods for enhancing post-ischemic functional recovery and/or providing other benefits through administration of mitochondria, and more specifically through administration of isolated mitochondria taken from cells that have been converted from somatic cells into pluripotent stem cells through techniques such as epigenetic reprogramming.

BACKGROUND

Ischemia can result from various physiologic events including myocardial infarction, abnormal cardiac rhythms such as tachycardia, bradycardia, etc., blood clots, atherosclerotic plaque rupture, coronary artery spasm and other blockage causing events. Ischemia can also result from certain medical procedures that involve temporary attenuation or obstruction of blood flow.

Mitochondria are essential organelles present in all nucleated cells whose main function is the generation of cellular ATP by oxidative phosphorylation. Mitochondria are also involved in a number of cellular pathways, including calcium homeostasis, apoptosis, heme biosynthesis, and cell signaling. The size, shape, and structural organization of mitochondria, as well as the number of these organelles per cell and their intracellular location, vary considerably depending on the organism, tissue, and physiological state of the cell examined. In the myocardium, mitochondria can constitute 30% of the total myocardial cell volume.

The human mitochondrial genome is a 16,569 base pair circular molecule. It consists of two strands, a guanine-rich strand (H-strand) and a cytosine-rich strand (L-strand).

It has been found that temporary attenuation or obstruction of blood flow can negatively alter myocardial mitochondrial structure and function. These structural and functional changes can persist even after normal blood flow resumes and can lead to decreased myocardial contractile function and myocardial survival.

SUMMARY

Embodiments herein include methods for enhancing post-ischemic functional recovery through administration of mitochondria and related devices and methods. In an embodiment, a method for enhancing post-ischemic functional recovery is included. The method can include harvesting somatic cells from a patient or a donor, converting the somatic cells into induced pluripotent stem cells, extracting mitochondria from the induced pluripotent stem cells, and transplanting the mitochondria into the patient.

In addition to one or more of the preceding or following aspects, or in the alternative to some aspects, in a second aspect, a method for enhancing post-ischemic functional recovery can include selecting a patient undergoing a procedure producing an ischemic condition.

In addition to one or more of the preceding or following aspects, or in the alternative to some aspects, in a third aspect, a method for enhancing post-ischemic functional recovery can include culturing the harvested somatic cells, expressing the transcription factors Oct4, Sox2, c-Myc, and Klf4 in the cultured somatic cells, identifying the induced pluripotent stem cells, selecting for the induced pluripotent stem cells, and culturing the induced pluripotent stem cells.

In addition to one or more of the preceding or following aspects, or in the alternative to some aspects, in a fourth aspect, a method for enhancing post-ischemic functional recovery can include culturing the somatic cells after the step of harvesting the somatic cells from the patient or the donor.

In addition to one or more of the preceding or following aspects, or in the alternative to some aspects, in a fifth aspect, a method for enhancing post-ischemic functional recovery can include culturing the induced pluripotent stem cells prior to the step of extracting mitochondria from the induced pluripotent stem cells.

In addition to one or more of the preceding or following aspects, or in the alternative to some aspects, in a sixth aspect, a method for enhancing post-ischemic functional recovery can include conditioning the induced pluripotent stem cells prior to the step of extracting mitochondria in order to enhance mitochondrial numbers or mitochondrial activity.

In addition to one or more of the preceding or following aspects, or in the alternative to some aspects, in a seventh aspect, a method for enhancing post-ischemic functional recovery can include conditioning the induced pluripotent stem cells by applying an electric field to the induced pluripotent stem cells.

In addition to one or more of the preceding or following aspects, or in the alternative to some aspects, in an eighth aspect, a method for enhancing post-ischemic functional recovery can include converting only a portion of the somatic cells into induced pluripotent stem cells, including extracting mitochondria from the remaining somatic cells, and transplanting mitochondria from the somatic cells into the patient or donor along with the mitochondria from the induced pluripotent stem cells.

In addition to one or more of the preceding or following aspects, or in the alternative to some aspects, in a ninth aspect, a method for enhancing post-ischemic functional recovery can include harvesting somatic cells from a patient or a donor, converting the somatic cells into induced pluripotent stem (iPS) cells, inducing the induced pluripotent stem cells to differentiate prior to the step of extracting mitochondria, extracting mitochondria from the differentiated cells, and transplanting the mitochondria into the patient or donor.

In addition to one or more of the preceding or following aspects, or in the alternative to some aspects, in a tenth aspect, a method for enhancing post-ischemic functional recovery can include culturing the differentiated cells prior to the step of extracting mitochondria from the differentiated cells.

In addition to one or more of the preceding or following aspects, or in the alternative to some aspects, in a eleventh aspect, a method for enhancing post-ischemic functional recovery can include conditioning the differentiated cells prior to the step of extracting mitochondria in order to enhance mitochondrial numbers or mitochondrial activity.

In addition to one or more of the preceding or following aspects, or in the alternative to some aspects, in a twelfth aspect, a method for enhancing post-ischemic functional recovery can include conditioning the differentiated cells by applying an electric field to the differentiated cells.

In addition to one or more of the preceding or following aspects, or in the alternative to some aspects, in a thirteenth aspect, a method for enhancing post-ischemic functional recovery can include inducing the iPS cells to differentiate into cardiomyocytes or non-pluripotent cardiomyocyte precursors.

In addition to one or more of the preceding or following aspects, or in the alternative to some aspects, in a fourteenth aspect, a method for enhancing post-ischemic functional recovery can include inducing the iPS cells to differentiate into hepatocytes or non-pluripotent hepatocyte precursors.

In addition to one or more of the preceding or following aspects, or in the alternative to some aspects, in a fifteenth aspect, a method for enhancing post-ischemic functional recovery can include inducing the iPS cells to differentiate into, cells of the digestive tract, lung cells, thyroid cells, adrenal cells, pancreatic islet cells, cells of the testes or ovaries, cardiomyocytes, skeletal myocytes, smooth muscle cells, hepatocytes, stomach cells, adipocytes, neurons, glial cells, retinal cells, osteoblasts, osteoclasts, renal cells, skin cells of the epidermis, skin cells of the dermis, red blood cells, white blood cells, or epithelial cells.

In addition to one or more of the preceding or following aspects, or in the alternative to some aspects, in a sixteenth aspect, a method for enhancing post-ischemic functional recovery can include harvesting somatic cells from a patient or a donor, extracting mitochondria from the somatic cells, reprogramming the mitochondria to achieve phenotypic changes associated with mitochondria in induced pluripotent stem cells, and transplanting the mitochondria into the patient.

In addition to one or more of the preceding or following aspects, or in the alternative to some aspects, in a seventeenth aspect, a method for enhancing post-ischemic functional recovery can include reprogramming the mitochondria via demethylation of mitochondrial DNA.

In addition to one or more of the preceding or following aspects, or in the alternative to some aspects, in a eighteenth aspect, a mitochondrial transplant device is included having an interior volume and a mixture disposed within the interior volume of the vessel. The mixture can include isolated mitochondria, wherein the isolated mitochondria are harvested from cells that are induced pluripotent stem cells or from differentiated cells that have been induced to differentiate starting from induced pluripotent stem cells and a liquid medium.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
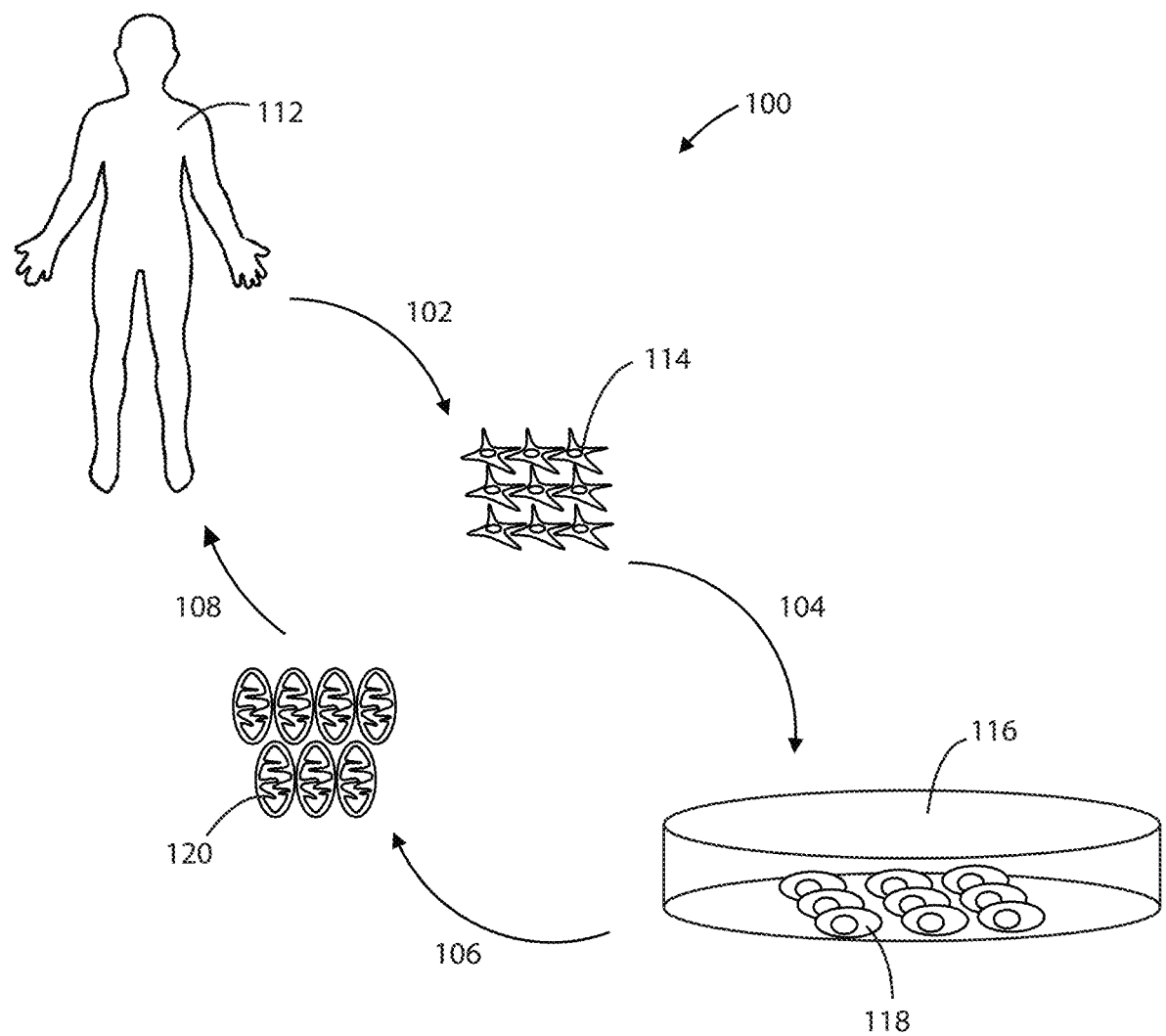
FIG. 1 is a flow chart illustrating operations of a method taken in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As referenced above, ischemia can negatively alter myocardial mitochondrial structure and function and these effects can persist even after normal oxygenation/blood flow resumes. One approach to addressing this issue is the transplantation of mitochondria to augment or replace mitochondria damaged by ischemia.

However, while not intending to be bound by theory, it is believed that epigenetic modifications may limit the therapeutic potential of transplanted mitochondria. The term "epigenetics" refers to heritable changes in gene expression that does not involve changes to the underlying DNA sequence. As such, epigenetic changes can relate to a change in phenotype without a change in genotype.

Epigenetic change is a regular and natural occurrence but can also be influenced by several factors including age, the environment/lifestyle, chronic stress, medication use and disease state. Epigenetic modifications can manifest as commonly as the manner in which cells terminally differentiate to end up as skin cells, liver cells, brain cells, etc. However, epigenetic change can have more damaging effects that can result in diseases like cancer. At least three systems including DNA methylation, histone modification and non-coding RNA (ncRNA)-associated gene silencing are currently considered to initiate and sustain epigenetic change.

In the process of creating a healthy embryo, the epigenetic tags associated with reproductive cells of the parents must be erased through a process referred to as "reprogramming". Reprogramming is a natural process that resets the epigenome of the early embryo so that it can form every type of differentiated cell needed in the body.

While not intending to be bound by theory, it is believed that reprogramming cells from which mitochondria are harvested can lead to benefits when those mitochondria are later transplanted. As such, embodiments herein relate to that transplantation of mitochondria that are obtained from cells that have been reprogrammed or otherwise converted into pluripotent stem cells ("induced pluripotent stem cells"

or "iPS cells"). In some embodiments, the mitochondria can be harvested from the iPS cells while they are in a pluripotent state. In other embodiments, the iPS cells can first be subjected to a treatment to cause them to differentiate (partially or fully) into a tissue-specific cell type such as myocardial cells and then the mitochondria can be harvested.

Referring now to FIG. 1, a flow diagram is shown of a method 100 utilizing undifferentiated induced pluripotent stem (iPS) cells for enhancing post-ischemic functional recovery in a patient in accordance with the embodiments herein. Method 100 can include harvesting somatic cells 114 from a patient 112 in operation 102. Method 100 can also include converting the somatic cells 114 into iPS cells 118 in operation 104. Method 100 can also include extracting mitochondria 120 from the iPS cells 118 in operation 106. Method 100 can also include transplanting the mitochondria 120 into the patient 112 in operation 108. Aspects of these steps are described in further detail below.

In some embodiments, methods herein can also include selecting a patient undergoing a procedure producing an ischemic condition. In some embodiments, the method includes selecting a patient undergoing a physiological event that produces or is likely to produce an ischemic condition. Such physiological events can include, but are not limited to, myocardial infarction, abnormal cardiac rhythms such as tachycardia, bradycardia, etc., blood clots, atherosclerotic plaque rupture, coronary artery spasm and other blockage causing events. Such ischemic conditions can include, but are not limited to, myocardial ischemia, neurological ischemia, bowel ischemia, hepatic ischemia, renal ischemia, etc. In some embodiments, the method can include identifying patients, or identifying a patient, that is exhibiting symptoms of an ischemic condition.

In some embodiments, methods herein can include selecting a patient undergoing a drug-induced event that produces an ischemic condition. Such drug-induced events can include, but are not limited to, drug-induced coronary vasospasm or drug-induced coronary artery thrombosis. Specific drugs that can result in these events can include, but are not limited to, cocaine, adrenergic B-agonists, sympathomimetics, phenylephrine, ergot alkaloids, triptans, enalapril, nifedipine, minoxidil, hydralazine, nitroprus side, adenosine, dipyridamole, HIV agents/protease inhibitors, rosiglitazone, estrogens, oral contraceptives, NSAIDS, COX-2 inhibitors, and the like. As such, in some embodiments, the method can include identifying patients, or identifying a patient, that is currently taking or has been taking any of these medications.

In some embodiments, methods herein can include selecting a patient undergoing a medical procedure that produces an ischemic condition. Such medical procedure can include any medical procedure that results in the blockage or attenuation of blood flow.

Such medical procedures can include, but are not limited to, CABG (coronary artery bypass graft), balloon angioplasty, transcutaneous medical device placement procedures including placement of stents, valves, grafts and the like, organ transplants, other cardiac procedures, and the like.

In some embodiments, methods herein can include transplant of mitochondria into tissues or organs stored for short durations prior to or during a medical procedure, or for long-term storage of tissues or organs using techniques such as cryopreservation.

In some embodiments, methods herein can include converting the somatic cells into iPS cells. Converting the somatic cells into iPS cells can include culturing the harvested somatic cells; expressing the transcription factors octamer-binding transcription factor 4 (Oct4), sex determining region Y-box 2 (Sox2), myelocytomatosis oncogene cellular homolog (c-Myc), and Krueppel-like factor 4 (Klf4) in the cultured somatic cells; identifying the iPS cells; selecting for the iPS cells; and culturing the iPS cells. In some embodiments, the iPS cells are cultured into a fully established iPS cell line.

In some embodiments, methods herein can include culturing the somatic cells after the step of harvesting the somatic cells from the patient. In some embodiments, the method includes culturing the iPS cells prior to the step of extracting mitochondria from the iPS cells. In some embodiments, the method includes conditioning the iPS cells prior to the step of extracting mitochondria in order to enhance mitochondrial numbers or mitochondrial activity. In some embodiments, conditioning the iPS cells prior to the step of extracting mitochondria can include applying an electric field to the cells. In some embodiments, conditioning the iPS cells can include applying growth factors, cytokines, or other small molecules to the cells. In some embodiments, conditioning the iPS cells can include subjecting the cells to a simulated milieu of a targeted environment, such as a targeted transplant environment. In some embodiments, conditioning the iPS cells can include subjecting the cells to mechanical strain either continuously or in a pulsed manner such as by simulating the mechanical strain associated with a heartbeat.

In some embodiments, methods herein include converting only a portion of the harvested somatic cells into iPS cells, extracting mitochondria from the remaining somatic cells, and transplanting the mitochondria from the somatic cells into the patient along with the mitochondria from the iPS cells.

Figure 2:
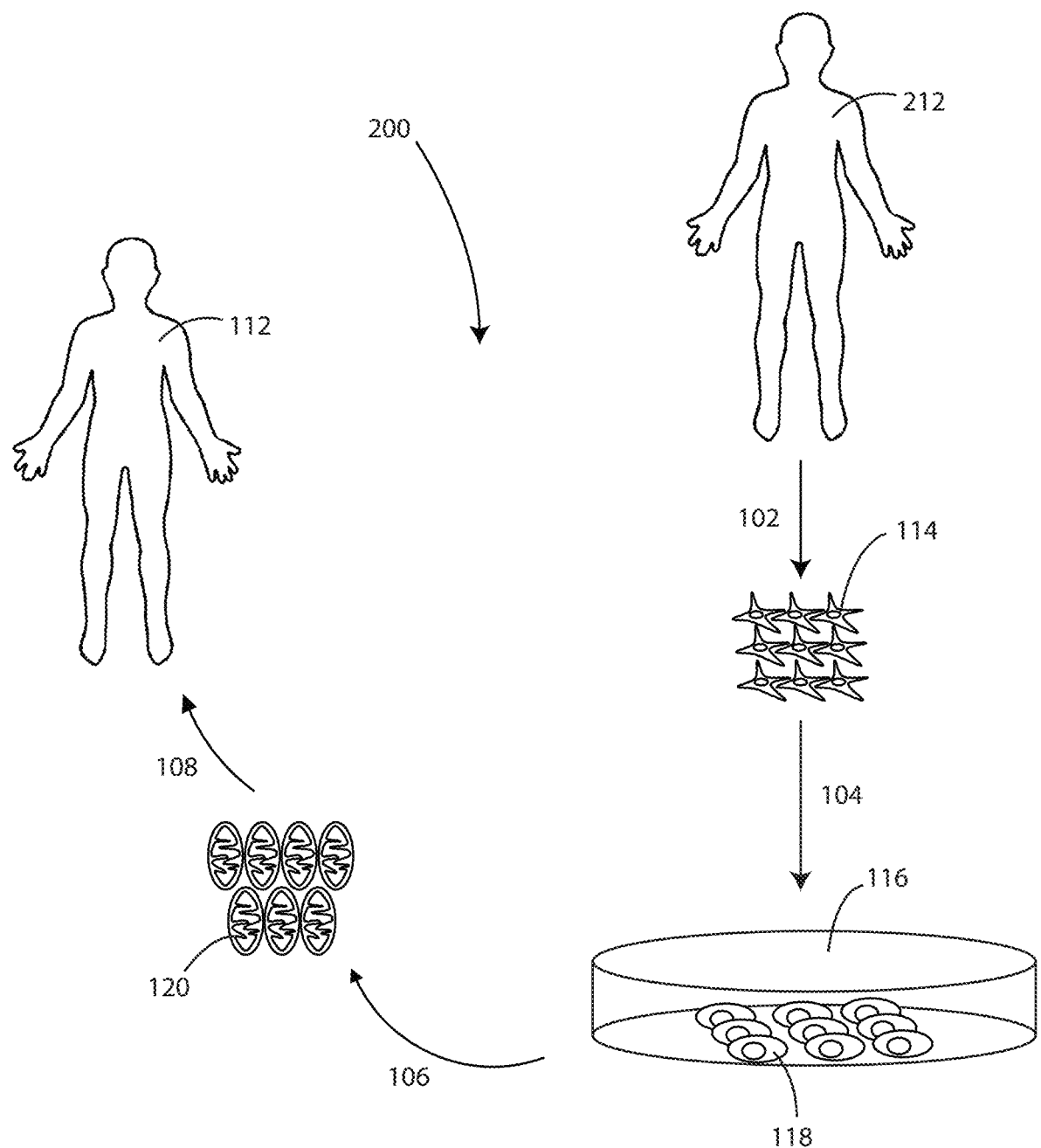
FIG. 2 is a flow chart illustrating operations of a method taken in accordance with various embodiments herein.

In some embodiments, the transplant of mitochondria can be autologous, such that the cells are harvested from the same patient that will be receiving the transplant later on (as illustrated in FIG. 2). This can be particularly effective in scenarios in which the timing of the ischemic event or procedure can be predicted. For example, in the context of a patient undergoing a medical procedure that will result, or has the risk of resulting, in an ischemic condition, cells (or a tissue sample generally) can be obtained from that patient in advance.

However, in some embodiments, the transplant of mitochondria can be non-autologous. For example, it can be more difficult to obtain cells from the patient in a manner so as to allow reprogramming of the cells and extraction of mitochondria. For example, in the context of a patient who experiences a sudden physiological event that results in an ischemic condition, it may be difficult or impossible to obtain a cell sample or tissue sample and process it in time to achieve a therapeutic benefit for that patient. As such, in some embodiments, cells or tissue can be harvested from a donor other than the patient who ultimately receives the mitochondrial transplant. Therefore, in some cases the transplant can be allogeneic or syngeneic. Referring to FIG. 2, a diagram of a non-autologous transplant method 200 is shown. FIG. 2 is similar to FIG. 1. However, instead of harvesting cells from the patient 112, the cells are harvested from a donor 212.

Figure 3:
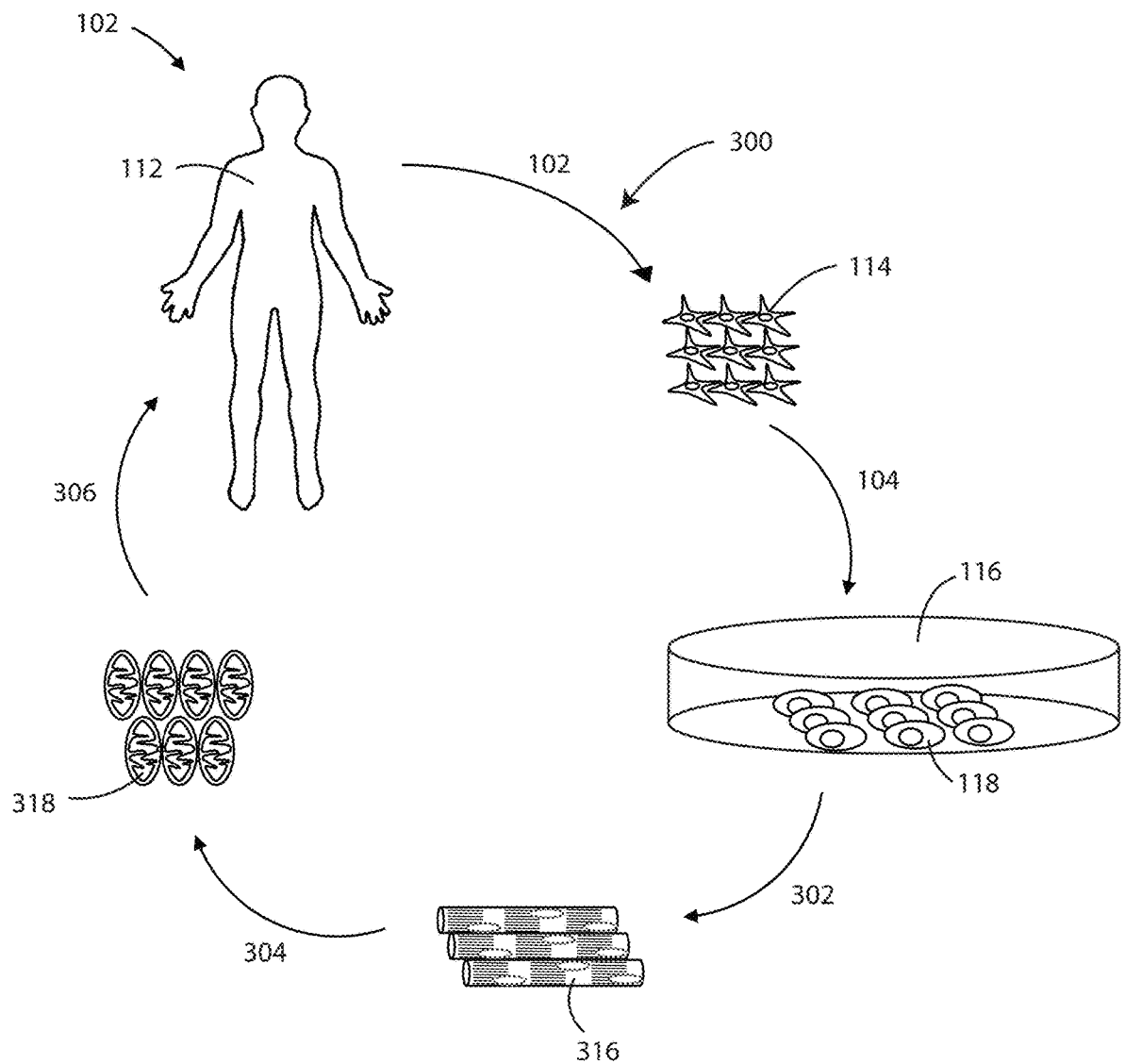
FIG. 3 is a flow chart illustrating operations of a method taken in accordance with various embodiments herein.

It will be appreciated that methods herein can vary from that shown in FIG. 1. For example, in some embodiments, after harvested somatic cells are converted into iPS cells, they can be induced to differentiate into a type of differentiated tissue prior to extraction of mitochondria. Referring now to FIG. 3, a flow diagram is shown of a method 300 utilizing differentiated iPS cells for enhancing post-ischemic functional recovery in a patient in accordance with the embodiments herein. Method 300 can include operations of harvesting somatic cells 114 from a patient 112 in operation 102. The method 300 can also include converting the somatic cells 114 into iPS cells 118 in operation 104. The method can also include inducing the iPS cells 118 to differentiate to form differentiated cells 316 in operation 302. The method can also include extracting mitochondria 318 from the differentiated cells 316 in operation 304. The method can also include transplanting the mitochondria 318 from the differentiated cells 316 into the patient 112 in operation 306.

In some embodiments, the method 300 includes selecting a patient undergoing a procedure producing an ischemic condition. In some embodiments, the method 300 includes selecting a patient undergoing a physiological ischemic event (e.g., myocardial infarction, stroke, bowel ischemia, hepatic ischemia, renal ischemia, exercise-induced myocardial ischemia, etc.) that produces an ischemic condition. In some embodiments, the method 300 includes selecting a patient undergoing a drug-induced event that produces an ischemic condition.

In some embodiments, the method 300 includes converting the somatic cells into iPS cells. Converting the somatic cells into iPS cells can include culturing the harvested somatic cells; expressing the transcription factors Oct4, Sox2, c-Myc, and Klf4 in the somatic cells; identifying the iPS cells; selecting for the iPS cells; and culturing the iPS cells. In some embodiments, the iPS cells are cultured into a fully established iPS cell line.

In some embodiments, the method 300 includes culturing the somatic cells after the step of harvesting the somatic cells from the patient. In some embodiments, the method 300 includes culturing the iPS cells prior to the step of differentiating the iPS cells. In some embodiments, the method 300 includes culturing the differentiated cells prior to the step of extracting mitochondria from the differentiated cells. In some embodiments, the method 300 includes conditioning the differentiated cells prior to the step of extracting mitochondria in order to enhance mitochondrial numbers or mitochondrial activity.

In some embodiments, inducing the iPS cells to differentiate includes inducing the iPS cells to differentiate into cardiomyocytes or non-pluripotent cardiomyocyte precursors. In some embodiments, inducing the iPS cells to differentiate includes inducing the iPS cells to differentiate into hepatocytes or non-pluripotent hepatocyte precursors.

In some embodiments, when iPS cells are differentiated into cardiomyocytes or non-pluripotent cardiomyocyte precursors, the conditioning step can include applying an electric field to the cells, applying growth factors, cytokines, or other small molecules to the cells, subjecting the cells to a simulated milieu of a targeted environment, such as a targeted transplant environment, and/or subjecting the cells to mechanical stretch or strain either continuously or in a pulsed manner such as by simulating the mechanical strain associated with a heartbeat.

It is noted that the iPS cells can be induced to differentiate into any of the other cell types representative of all three germ layers—the endoderm, the ectoderm, and the mesoderm. The iPS cells can be induced to differentiate to include, but not be limited to, cells of the digestive tract, lung cells, thyroid cells, adrenal cells, pancreatic islet cells, cells of the testes or ovaries, skeletal myocytes, smooth muscle cells, stomach cells, adipocytes, neurons, glial cells, retinal cells, osteoblasts, osteoclasts, renal cells, skin cells, red blood cells, white blood cells, epithelial cells, etc., or any of their non-pluripotent progenitor cells.

Figure 4:
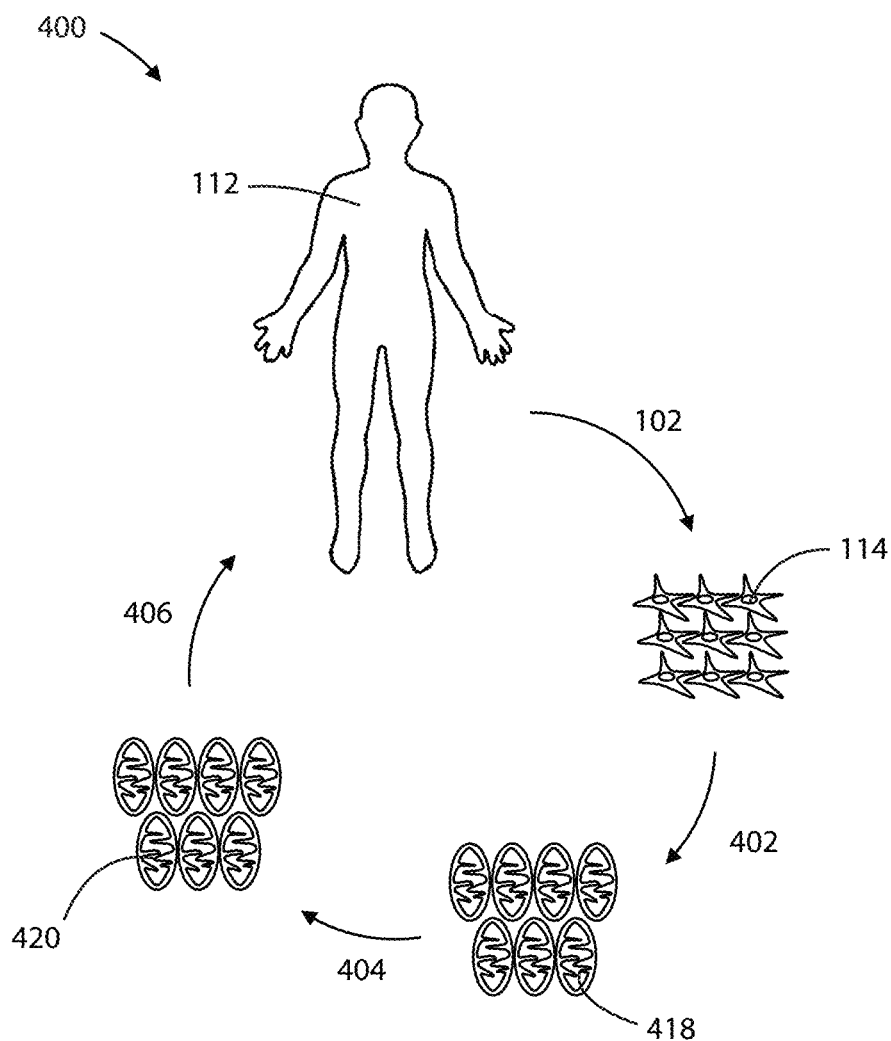
FIG. 4 is a flow diagram of a method for enhancing post-ischemic functional recovery in accordance with the embodiments herein.

In some embodiments, mitochondria can be reprogrammed after their extraction from cell(s). Referring now to FIG. 4, a flow diagram is shown of a method 400 for enhancing post-ischemic functional recovery in accordance with the embodiments herein. The method 400 can include steps of harvesting somatic cells 114 from a patient in operation 102. The method can further include extracting mitochondria 418 from the somatic cells 114 in operation 402. The method can further include reprogramming the mitochondria 418 to achieve phenotypic changes associated with mitochondria 418 in iPS cells in operation 404. The method can further include transplanting the reprogrammed mitochondria 420 into the patient 112 in operation 406. In some embodiments, reprogramming the mitochondria comprises demethylation of mitochondrial DNA.

Harvesting Somatic Cells

A wide variety of somatic cell types can be used in accordance with the embodiments herein. In some embodiments, it may be advantageous to harvest somatic cells from locations that allow for the use of minimally invasive techniques. Somatic cells that can be harvested from such locations include, but are not limited to, the following: skin cells from a routine skin biopsy; cheek epithelial cells from a buccal swab; blood cells from a blood specimen; renal tubular fibroblasts from a urine specimen; skeletal muscle cells from a muscle punch biopsy; and hair follicle keratinocytes from a hair specimen. It will be appreciated that other somatic cell types can be harvested from other locations in a body that require more invasive techniques that include, but are not limited to, cardiac muscle cells, stomach cells, liver cells, spleen cells, pancreatic islet cells, lung cells, bone cells, neurons, adipocytes, chondrocytes, and the like. In some embodiments somatic cells can be harvested from a mammal. In some embodiments, somatic cells can be harvested from a human.

Careful processing of harvested tissue and cells can be important to creating a uniform population of cells. Removal of connective tissue and larger unwanted material can be performed by the process of mechanical dissection. Various enzymatic and mechanical techniques can be used to further dissociate the somatic cells of interest from the surrounding tissue. Enzymes such as trypsin, pepsin, collagenase, etc. can be used to remove unwanted extracellular material from the harvested sample. Additional separation techniques such as differential centrifugation, differential filtration, and FACS analysis can also be used to isolate a specific somatic cell population from a heterogeneous tissue or cell sample.

Converting Somatic Cells into iPS Cells

The conversion of somatic cells into iPS cells can be accomplished by utilizing specific factors shown to be effective in converting differentiated cells back to a pluripotent state. According to the methods of Takahashi and Yamanaka, Cell 126, 663-676, 2006, the use of at least the transcription factors Oct4, Klf4, Sox2, and c-Myc has been shown to be effective in creating iPS cells from a variety of somatic cell types. The result of converting somatic cells to iPS cells can also result in reprogramming of mitochondria within the cell. Aspects of converting somatic cells into iPS cells are described in U.S. Pat. No. 8,058,065, the content of which is herein incorporated by reference.

Mitochondrial reprogramming that results from converting somatic cells to iPS cells can be characterized by changes in the mitochondrial phenotype. Phenotypic changes that can be observed during mitochondrial reprogramming in a cell can include changes in mitochondrial morphology, ultrastructure, mitochondria number and activity, mtDNA integrity, mitochondrial metabolism, and mtDNA epigenetics, such as mtDNA methylation or demethylation.

The conversion of somatic cells into iPS cells can include introduction of the genetic material (i.e., DNA or RNA) encoding the desired transcription factors using a variety of methods, and can be tailored dependent on which type of somatic cell is selected for conversion. In some cases, the use of retroviral and lentiviral vectors can result in the stable integration of the genetic material into the host genome of the somatic cells. Retroviral and lentiviral transduction techniques result in a constitutively active expression of the transcription factors within the cells. In some cases, inducible retroviral and lentiviral vectors can be used to provide more stringent control over the expression of the transcription factors using antibiotic selection. Additional methods for integrating genetic material into the host genome of the somatic cells can include Cre-LoxP recombination systems and transposon-based integration systems.

Other non-integrating methods for introducing genetic material into somatic cells can also be employed. In some embodiments, the use of Sendai virus can introduce genetic material encoding the transcription factors into the somatic cells. One distinct advantage of using Sendai virus is that it does not result in the integration of the genetic material into the host genome, and rather accomplishes expression of the transcription factors entirely in the cytoplasm of the cells, without disruption of the host genome. Additional methods of non-integrating introduction of genetic material include the use of adenovirus vectors, adeno-associated viral vectors, and a variety of plasmid expression vectors.

In some embodiments, protein transfection techniques can be utilized to deliver the desired transcription factors into the somatic cells to induce differentiation without the use of genetic material.

Extracting Mitochondria from Cells

Mitochondria can be extracted from (or isolated from) cells or tissue directly harvested from a patient or from cells obtained out of cell culture. Mitochondria can also be harvested directly from iPS cells. In some embodiments, the process of extracting mitochondria from cells or tissue begins with separating the mitochondria from the rest of the cellular material. In the case of a tissue sample harvested from a patient, cells can be separated from the surrounding extracellular material either through enzymatic or mechanical techniques, or both. Mechanical separation techniques that result in the release into solution of intact cellular organelles, such as mitochondria, are desired. In some cases, mechanical separation of cells from a tissue sample can include use of mortars and pestles, blenders, Dounce homogenizers, syringes and needles, ultrasonifcation, etc. In some cases, commercial isolation kits such as the Qproteome™ Mitochondria Isolation kit (Qiagen, Valencia, Calif.), can be used to isolate mitochondria. In some cases, mechanical separation can also be used to lyse the cell membranes of cell culture samples. In some cases, cells can be lysed using cell lysis and extraction buffer designed to break open the cell membranes and release intact mitochondria into solution for further purification.

It will be appreciated that in some embodiments, differential centrifugation can be utilized to separate the mitochondrial fraction of a tissue sample or cell culture sample from the rest of the tissue or cellular material. Differential centrifugation is a separation technique that functions on the principle that larger cellular and extracellular material will sediment out of solution under lower centrifugal forces and smaller material will sediment out of solution under higher centrifugal forces. Mitochondria are typically found to be around 0.5-10 µm in size.

It will be appreciated that in some embodiments, differential filtration methods can be used to separate mitochondria from tissue or cells samples. In differential filtration, a homogenized cellular sample can be passed through successively smaller porous filters to separate the mitochondrial fraction from the rest of the cellular material.

Mitochondrial fractions completely extracted from tissue or cell samples can be suspended in mitochondrial respiration buffer prior to further use. Aspects regarding isolating mitochondria can be found in published application number PCT/US2015/035584 (WO2015/192020), and in U.S. Pat. No. 7,407,800, the content of which is herein incorporated by reference.

Transplanting Mitochondria into a Patient

Transplanting mitochondria into a patient can occur by a variety of techniques. In some embodiments, when it is desired to transplant mitochondria into an ischemic region of the heart, the mitochondria can be transplanted by direct injection into the ischemic myocardium using a syringe or similar device. In some embodiments, the mitochondria can be injected into one or more locations surrounding and within the ischemic myocardium. In some embodiments, mitochondria can be transplanted into ischemic myocardium through intracoronary infusion via the coronary arteries. In some embodiments, transplanting mitochondria can occur during open heart surgery or during thoracotomy. In some embodiments, mitochondria can be injected into the ischemic tissue or surrounding vasculature of the ischemic tissue of the kidney, liver, pancreas, skeletal muscle, or lungs. In some embodiments, mitochondria are injected at a plurality of sites. In some embodiments, a solution of mitochondria and a buffer are prepared such that the concentration of mitochondria is between about $2 \times 10^5$ to $2 \times 10^8$ mitochondria per milliliter. In some embodiments, the amount injected is between 0.05 mL and 0.3 mL per injection site. In some embodiments, the amount injected is about 0.1 mL per injection site.

The mitochondria, disposed within a suitable medium, can be temporarily stored in a vessel such as a bag, pouch, syringe or cannula barrel, or the like. In various embodiments herein, a mitochondrial transplant device is included. The mitochondrial transplant device can include a vessel defining an interior volume. A mixture of mitochondria and a suitable medium can be disposed within the interior volume of the vessel. The total volume of the mixture of mitochondria and the suitable medium can be from about 0.05 ml to about 1000 ml. In some embodiments, the total volume of the mixture of mitochondria and the suitable medium can be from about 0.1 ml to about 50 ml.

Figure 5:
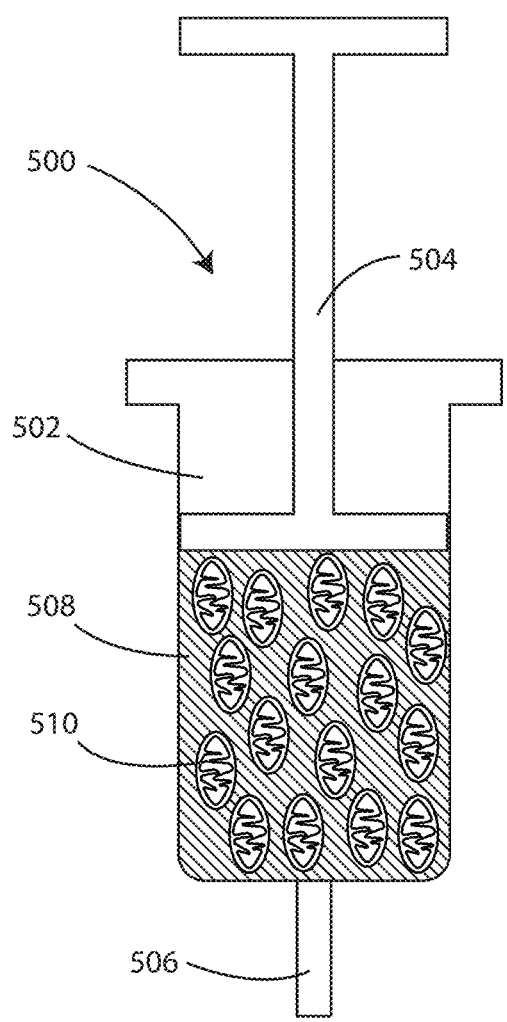
FIG. 5 is a schematic view of a mitochondrial transplant device in accordance with various embodiments herein.
Figure 6:
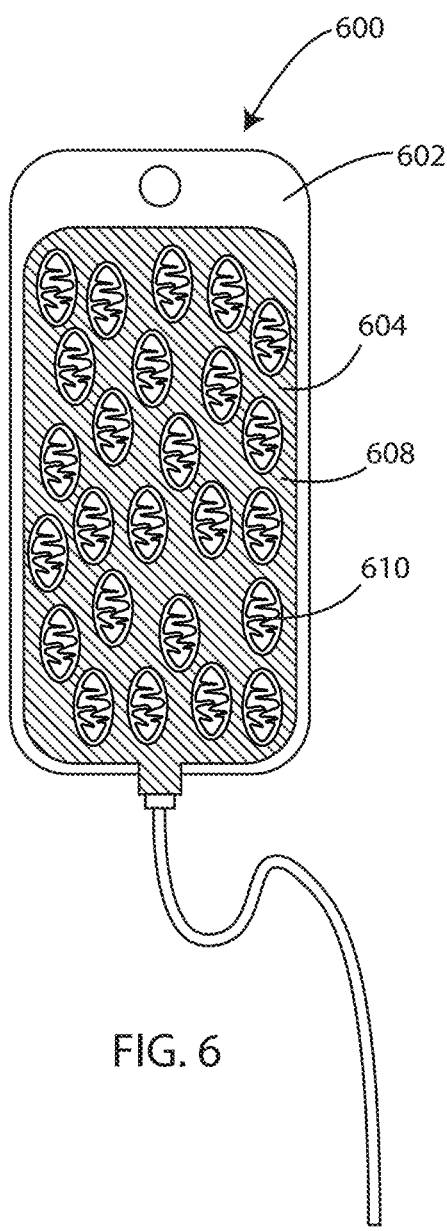
FIG. 6 is a schematic view of a mitochondrial transplant device in accordance with various embodiments herein.

Referring now to FIG. 5, a mitochondrial transplant device 500 is shown in accordance with various embodiments herein. The transplant device 500 can include a barrel 502 and a plunger 504. The barrel 502 can define an interior volume into which a mixture of mitochondria 510 and a suitable medium 508 can be disposed. It will be appreciated that the device can take on many different specific forms. Referring now to FIG. 6, another mitochondrial transplant device 600 is shown in accordance with various embodiments herein. Mitochondrial transplant device 600 can include a bag 602 defining an interior volume 604. A mixture of mitochondria 510 and a suitable medium 508 can be disposed within the interior volume 604 of the bag 602.

In some embodiments, the medium of the mixture can be a buffer. In some embodiments, the buffer can be a respiration buffer. Buffers can include various components including, but not limited to, sugars, such as sucrose, salts such as monopotassium phosphate, magnesium chloride, glutamate, malate, succinate, and other components such as HEPES buffer, EGTA (ethylene glycol-bis(β-aminoethyl ether)-N, N,N',N'-tetraacetic acid), adenosine diphosphate (ADP), and the like. In a particular embodiment, the respiration buffer can include approximately 250 mmol/l sucrose, 2 mmol/l $KH_2PO_4$, 10 mmol/l $MgCl_2$, 20 mmol/l $K^+$-HEPES buffer, pH 7.2, 0.5 mmol/l $K^+$-EGTA, pH 8.0, 5 mmol/l glutamate, 5 mmol/i malate, 8 mmol/l succinate, and 1 mmol/l ADP.

Culturing Cells

The culture of somatic cells isolated from a patient, or iPS cells created by converting somatic cells, can be accomplished in the laboratory using established cell culture techniques. Cell culture medium and conditions can be selected on the basis of the cell type being propagated. Various supplements required for growth are tissue specific and include, but are not limited to, growth factors, cytokines, serum-containing medium, serum-free medium, oxygen, carbon dioxide, antibiotics, surfactants, amino acids, etc. In some cases, conditioned medium from a feeder cell culture may be used to provide nutrients and secreted factors to the cultured cells. In some cases, iPS cells can be cultured along with a feeder cell population.

Cells can be cultured in a variety of cell culture vessels and environments. In some embodiments, the cell culture vessel can include a coated or uncoated flat-bottomed plastic dish or flask. In some embodiments, the cell culture vessel can include a roller bottle, spinner flask, hollow-fiber cell culture system, or fermentation vessel. Temperature and humidity can be controlled during culture of cells. In some cases, the temperature of the incubation is at or about 37 degrees Celsius. In some cases, the temperature of the incubation is at or about 25-45 degrees Celsius. In some embodiments, the humidity of the incubation source is kept at or about 5%. In some embodiments, the humidity of the incubation source is kept at or about 0-20%.

Maintenance of the cells in culture requires regular subculturing. Regular subculturing of the cell population ensures that the cells maintain exponential growth and sufficient nutrients available for sustaining a healthy, viable culture. In some embodiments, cells are subcultured every 24 hours. In some embodiments, cells are subcultured every 24-48 hours. In some embodiments, cells are grown to 80% confluency. In some embodiments, cells are grown to 100% confluency.

Selecting Patients and Classes of Patients

Selecting a patient who will benefit from the methods embodied herein can involve selecting those individuals undergoing or having undergone a procedure or event producing an ischemic condition. Ischemia can occur within an organ or a tissue of a patient based on a variety of causes. In some cases, patients can be selected from those undergoing open heart surgery or thoracotomy, which can cause an ischemic event at a localized region of the heart muscle. In some cases, patients can be selected from those undergoing a physiological ischemic event (e.g., myocardial infarction, stroke, bowel ischemia, hepatic ischemia, renal ischemia, exercise-induced myocardial ischemia, etc.) that produces an ischemic condition in tissue or an organ. In some embodiments, patients can be selected from those undergoing a drug-induced event that produces an ischemic condition. In some embodiments, patients can be selected from those experiencing ischemia to the heart, liver, skeletal muscle, pancreas, kidney, or lungs.

In some cases, mitochondrial transplant in accordance with the embodiments herein can benefit patients with any one of a number of mitochondrial diseases, mitochondrial myopathy, and related disorders. In some embodiments, mitochondrial transplant in accordance with the embodiments herein can be used to enhance athletic performance.

There are various markers of mitochondrial function. By way of example, cytochrome oxidase is believe to be an indicator of impaired mitochondrial function. In specific, cytochrome oxidase mRNA levels can be measured and a decrease can indicate of impaired mitochondrial function. As another example, cytochrome oxidase activity itself can be measured and a decrease in activity can indicate of impaired mitochondrial function. In some embodiments, the method can include evaluating the patient for markers of mitochondrial function. In some embodiments, the method can include measuring cytochrome oxidase mRNA levels. In some embodiments, the method can include measuring cytochrome oxidase activity.

Conditioning Cells for Enhanced Mitochondrial Numbers/Function

It will be appreciated that conditioning of differentiated cells to enhance mitochondrial numbers or mitochondrial activity can be dependent upon the type of differentiated cells created. In some embodiments, when iPS cells are differentiated into cardiomyocytes or skeletal myocytes, the conditioning step can include applying an electric field to the cells, applying growth factors, cytokines, or other small molecules to the cells, subjecting the cells to a simulated milieu of a targeted environment, such as a targeted transplant environment, and/or subjecting the cells to mechanical stretch or strain either continuously or in a pulsed manner such as by simulating the mechanical strain associated with a heartbeat.

In some cases, external forces or agents, such as growth factors, transcription factors, replication factors, enzymes, hormones, co-factors, small molecules, sugars, drug compounds, DNA, RNA, proteins, etc. may also be applied externally or internally to condition differentiated cells, and is dependent on the cell type.

Mitochondrial number and mitochondrial activity can be determined by a variety of biochemical and molecular biology methods. In some cases, the mitochondrial number can be determined by hemocyotometry, quantification of mitochondrial DNA (mtDNA), mitochondrial mass determination, or other molecular visualization techniques such as confocal microscopy, electron microscopy, or live-cell imaging microscopy, etc. In some embodiments, mitochondrial number can be determined by commercially available kits. In some cases, mitochondrial activity can be determined in vitro by enzymatic reporter assays, high-resolution respirometery, or flow cytometry, etc.

Differentiating iPS Cells into Cardiomyocytes or Non-Pluripotent Precursors

The process of differentiating iPS cells into any of the cell types that are representative of all three germ layers can be dependent on the desired cell type. In some embodiments, the process of directed differentiation of iPS cells into cardiomyocytes or their non-pluripotent precursors includes manipulation of the Wnt, Activin, Nodal, TGFβ, BMP, and FGF signaling pathways and growth factors involved in the differentiation process. In some embodiments, the process of directed differentiation of iPS cells into cell types such as cells of the digestive tract, lung cells, thyroid cells, adrenal cells, pancreatic islet cells, cells of the testes or ovaries, skeletal myocytes, smooth muscle cells, hepatocytes, stomach cells, adipocytes, neurons, glial cells, retinal cells, osteoblasts, osteoclasts, renal cells, skin cells of the epidermis, skin cells of the dermis, red blood cells, white blood cells, epithelial cells, etc., or any of their non-pluripotent progenitor cells can be tailored by manipulation of cell signaling pathways responsible for terminal differentiation into any one of the desired cell types. Techniques for differentiating pluripotent stems cells into differentiated cells are described in US2015/0299658, the content of which is herein incorporated by reference.

Reprogramming Mitochondria Directly

Mitochondrial DNA (mtDNA) is maternally inherited and non-nuclear in nature. The mtDNA encodes 13 subunit proteins found in the respiratory chain and 24 non-coding genes specific to RNA. Epigenetic modifications, such as DNA methylation, found in nuclear DNA are likewise found in mtDNA. DNA methylation occurs when a methyl group is added to the DNA nucleotides cytosine or adenine, and it does not alter the mtDNA sequence. DNA demethylation occurs through the mechanisms of DNA repair, including those responsible for base excision repair.

In some embodiments, mtDNA is reprogrammed directly within mitochondria isolated from somatic cells. In some embodiments, reprogramming of mtDNA can involve incubation of the isolated mitochondria with various DNA repair enzymes that contain coding sequences that target their delivery into the mitochondria and result in mtDNA demethylation. In some embodiments, reprogramming of the mtDNA can involve transfection of mitochondria with genetic material encoding DNA repair enzymes that result in mtDNA demethylation. In some embodiments, reprogramming of the mtDNA can involve transfection of mitochondria using viral vectors such as adenovirus, adeno-associated virus, and the like to introduce genetic material encoding DNA repair enzymes that result in mtDNA demethylation.

Reprogramming of the mitochondria directly or conversion of somatic cells into iPS cells can introduce mtDNA mutations. In some embodiments, mtDNA can be sequenced to determine the mtDNA integrity following the mitochondrial or cellular reprogramming event. In some embodiments, mitochondrial gene arrays may be performed to determine gene expression or mtDNA sequence anomalies that may arise during reprogramming or cellular conversion events.

Aspects may be better understood with reference to the following examples. These examples are intended to be representative of specific embodiments, but are not intended as limiting the overall scope of embodiments herein.

EXAMPLES

Example 1: Reprogramming Somatic Cells and Extracting the Mitochondria

A tissue sample is obtained from a patient. The tissue sample contains somatic cells. The tissue sample is dissected and the cells are isolated.

The cells are then reprogrammed to the methods of Takahashi and Yamanaka, Cell 126, 663-676, 2006. In specific, four factors (Oct3/4, Sox2, c-Myc, and Klf4) were introduced under embryonic stem cell culture conditions.

The tissue is homogenized in a volume of 5 mL of an isolation buffer (300 mmol/L sucrose, 10 mmol/L HEPES-KOH, 1 mmol/L EGTA-KOH, pH 7.4) and then treated to 10 min of Subtilisin A enzymatic digestion on ice. The digested tissue is then filtered through a series of filters (40, 40 and 10 uM), pre-wetted with isolation buffer, and the mitochondria are subsequently precipitated by centrifugation at 9×g for 10 min at 4° C.

The mitochondria are counted by hemocytometer or by particle counter. The mitochondria are then suspended in freshly prepared respiration buffer (250 mmol/l sucrose, 2 mmol/l $KH_2PO_4$, 10 mmol/l $MgCl_2$, 20 mmol/l $K^+$-HEPES buffer, pH 7.2, 0.5 mmol/l $K^+$-EGTA, pH 8.0, 5 mmol/l glutamate, 5 mmol/l malate, 8 mmol/l succinate, and 1 mmol/l ADP).

Example 2: Transplanting Induced Pluripotent Mitochondria into a Patient

Mitochondria, as prepared above are suspended in a respiration buffer. The mitochondria and respiration buffer are then mixed (at approximately $2 \times 10^7$ cells per ml) and injected into a patient using a syringe (tuberculin syringe with a standard 18 G needle). In specific, the mixture was injected into an ischemic myocardium at a plurality of sites at 0.1 mL per site.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A method for enhancing post-ischemic functional recovery of a patient after an ischemic event or an ischemic condition comprising:
   harvesting somatic cells from a patient or a donor;
   converting the somatic cells into induced pluripotent stem cells;
   extracting mitochondria from the induced pluripotent stem cells; and
   transplanting the mitochondria into the patient.

2. The method of claim 1, further comprising selecting a patient undergoing a procedure producing an ischemic condition.

3. The method of claim 1, wherein converting the somatic cells into induced pluripotent stem cells comprises the steps of:
   culturing the harvested somatic cells;
   expressing the transcription factors Oct4, Sox2, c-Myc, and Klf4 in the cultured somatic cells;
   identifying the induced pluripotent stem cells;
   selecting for the induced pluripotent stem cells; and
   culturing the induced pluripotent stem cells.

4. The method of claim 1, further comprising culturing the somatic cells after the step of harvesting the somatic cells from the patient or the donor.

5. The method of claim 1, further comprising culturing the induced pluripotent stem cells prior to the step of extracting mitochondria from the induced pluripotent stem cells.

6. The method of claim 1, further comprising conditioning the induced pluripotent stem cells prior to the step of extracting mitochondria in order to enhance mitochondrial numbers or mitochondrial activity.

7. The method of claim 6, wherein conditioning the induced pluripotent stem cells comprises:
applying an electric field to the induced pluripotent stem cells.

8. The method of claim 1, wherein only a portion of the somatic cells are converted into induced pluripotent stem cells, the method further comprising
extracting mitochondria from the remaining somatic cells, and
transplanting mitochondria from the somatic cells into the patient or donor along with the mitochondria from the induced pluripotent stem cells.

9. A method for enhancing post-ischemic functional recovery comprising:
harvesting somatic cells from a patient or a donor;
converting the somatic cells into induced pluripotent stem (iPS) cells;
inducing the induced pluripotent stem cells to differentiate prior to the step of extracting mitochondria;
extracting mitochondria from the differentiated cells; and
transplanting the mitochondria into the patient or donor.

10. The method of claim 9, further comprising selecting a patient undergoing a procedure producing an ischemic condition.

11. The method of claim 9, wherein converting the somatic cells into induced pluripotent stem cells comprises the steps of
culturing the harvested somatic cells;
expressing the transcription factors Oct4, Sox2, c-Myc, and Klf4 in the cultured somatic cells;
identifying the induced pluripotent stem cells;
selecting for the induced pluripotent stem cells; and
culturing the induced pluripotent stem cells.

12. The method of claim 9, further comprising culturing the somatic cells after the step of harvesting the somatic cells from the patient or donor.

13. The method of claim 9, further comprising culturing the differentiated cells prior to the step of extracting mitochondria from the differentiated cells.

14. The method of claim 9, further comprising conditioning the differentiated cells prior to the step of extracting mitochondria in order to enhance mitochondrial numbers or mitochondrial activity.

15. The method of claim 9, wherein conditioning the induced pluripotent stem cells comprises:
applying an electric field to the induced pluripotent stem cells.

16. The method of claim 9, wherein inducing the iPS cells to differentiate comprises inducing the iPS cells to differentiate into cardiomyocytes or non-pluripotent cardiomyocyte precursors.

17. The method of claim 1, wherein converting the somatic cells into induced pluripotent stem cells results in one or more phenotypic changes within mitochondria of the somatic cells.

18. The method of claim 1, wherein the one or more phenotypic changes comprise changes in mitochondrial morphology, ultrastructure, number and activity, mtDNA integrity, mitochondrial metabolism, and mtDNA epigenetics.

19. The method of claim 1, wherein the method enhances mitochondrial function of the patient, wherein mitochondrial function is assessed based on at least one of measuring cytochrome oxidase mRNA levels and cytochrome oxidase activity.

20. A method for enhancing mitochondrial function of a patient comprising:
harvesting somatic cells from a patient or a donor;
converting the somatic cells into induced pluripotent stem cells;
extracting mitochondria from the induced pluripotent stem cells; and
transplanting the mitochondria into the patient;
wherein mitochondrial function is assessed based on at least one of cytochrome oxidase mRNA levels and cytochrome oxidase activity.

* * * * *